US009732121B2

(12) United States Patent
Foung et al.

(10) Patent No.: US 9,732,121 B2
(45) Date of Patent: Aug. 15, 2017

(54) RATIONAL VACCINE DESIGN FOR HEPATITIS C VIRUS

(71) Applicants: The Board of Trustees of the Leland Stanford Junior University, Stanford, CA (US); Thomas R. Fuerst, Damestown, MD (US)

(72) Inventors: Steven Foung, Stanford, CA (US); Zhen-Yong Keck, Redwood City, CA (US); Thomas R. Fuerst, Damestown, MD (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/493,153

(22) Filed: Sep. 22, 2014

(65) Prior Publication Data

US 2015/0086580 A1 Mar. 26, 2015

Related U.S. Application Data

(60) Provisional application No. 61/882,508, filed on Sep. 25, 2013.

(51) Int. Cl.
*A61K 39/29* (2006.01)
*C07K 14/005* (2006.01)
*C12N 7/00* (2006.01)
*A61K 39/12* (2006.01)
*A61K 39/00* (2006.01)

(52) U.S. Cl.
CPC ............ *C07K 14/005* (2013.01); *A61K 39/12* (2013.01); *C12N 7/00* (2013.01); *A61K 2039/55572* (2013.01); *A61K 2039/57* (2013.01); *C12N 2770/24222* (2013.01); *C12N 2770/24234* (2013.01)

(58) Field of Classification Search
None
See application file for complete search history.

(56) References Cited

U.S. PATENT DOCUMENTS

| 7,879,326 | B2 | 2/2011 | Foung et al. |
| 2002/0119495 | A1* | 8/2002 | Nakano ................ A61K 38/162 435/7.1 |
| 2013/0084301 | A1 | 4/2013 | Foung et al. |

OTHER PUBLICATIONS

Yi et al. Delineation of Regions Important for Heteromeric Association of Hepatitis C Virus E1 and E2. Virol. 1997; 231: 119-129.*
Slater-Handshy et al. HCV E2 glycoprotein: mutagenesis of N-linked glycosylation sites and its effects on E2 expression and processing. Virol. 2004; 319: 36-48.*

(Continued)

*Primary Examiner* — Janet L Andres
*Assistant Examiner* — Stuart W Snyder
(74) *Attorney, Agent, or Firm* — Pamela J. Sherwood; Bozicevic, Field & Francis LLP

(57) ABSTRACT

Compositions and methods are provided relating to HCV E2 protein and modifications thereto which enhance the immunogenicity of the protein for vaccine development with respect to the generation of a neutralizing immune response.

7 Claims, 7 Drawing Sheets
(4 of 7 Drawing Sheet(s) Filed in Color)

(56) References Cited

OTHER PUBLICATIONS

Zhang et al. Tracking global patterns of N-linked glycosylation site variation in highly variable viral glycoproteins: HIV, SIV, and HCV envelopes and influenza hemagglutinin. Glycobiology 2004; 14(12): 1229-1246.*

Xiang et al. Recombinant Hepatitis C Virus-Like Particles Expressed by Baculovirus: Utility in Cell-Binding and Antibody Detection Assays. J. Med. Virol. 2002; 68(4): 537-543.*

Bartosch; et al., "Infectious hepatitis C virus pseudo-particles containing functional E1-E2 envelope protein complexes.", J Exp Med. (Mar. 2003), 197(5):633-42.

Cai; et al., "Robust production of infectious hepatitis C virus (HCV) from stably HCV cDNA-transfected human hepatoma cells.", J Virol. (Nov. 2005), 79(22):13963-73.

Dorner; et al., "A genetically humanized mouse model for hepatitis C virus infection.", Nature (Jun. 2011), 474 (7350):208-11.

Hsu; et al., "Hepatitis C virus glycoproteins mediate pH-dependent cell entry of pseudotyped retroviral particles.", Proc NAtl Acad Sci USA. (Jun. 2003), 100(12):7271-6.

Lavillette; et al.,"Human serum facilitates hepatitis C virus infection, and neutralizing responses inversely correlate with viral replication kinetics at the acute phase of hepatitis C virus infection.", J Virol. (May 2005), 79(10);6023-34.

Law; et al., "Broadly neutralizing antibodies protect against hepatitis C virus quasispecies challenge.", Nat Med (Jan. 2008), 14(1):25-7.

Lindenbach; et al., "Complete replication of hepatitis C virus in cell culture.", Science (Jul. 2005), 309(5734):623-6.

Meuleman; et al., "Anti-CD81 antibodies can prevent a hepatitis C virus infection in vivo.", Hepatology (Dec. 2008), 48(6):1761-8.

Osburn; et al., Spontaneous control of primary hepatitis C virus infection and immunity against persistent reinfection., Gastroenterology (Jan. 2010), 138(1):315-24.

Pantophlet; et al., "Hyperglycosylated mutants of human immunodeficiency virus (HIV) type 1 monomeric gp120 as novel antigens for HIV vaccine design.", J Virol. (May 2003), 77(10):5889-901.

Pestka; et al., "Rapid induction of virus-neutralizing antibodies and viral clearance in a single-source outbreak of hepatitis C.", Proc Natl Acad Sci USA (Apr. 2007), 104(14):6025-30.

Szczepanek; et al., "Xenoepitope substitution avoids deceptive imprinting and broadens the immune response to foot-and-mouth disease virus.", Clin Vaccine Immunol. (Apr. 2012) 19(4):461-7.

Wakita; et al., "Production of infectious hepatitis C virus in tissue culture from a cloned viral genome.", Nat. Med. (Jul. 2005), 11(7):791-6.

Zhong; et al., "Robust hepatitis C virus infection in vitro.", Proc Natl Acad Sci USA (Jun. 2005), 102(26):9294-9.

* cited by examiner

Figure 3

| HCVpp | HMAbs | | | | | | | |
|---|---|---|---|---|---|---|---|---|
| | CBH4D | CBH4G | CBH-5 | HC-11 | HC-1 | CBH-7 | CBH-23 | R04 |
| H77c core-E1E2 | 0.84 | 5.43 | 4.00 | 1.90 | 0.69 | 0.24 | 0.17 | NB* |
| H77c core-E1ΔHVR1E2 | 0.48 | 5.29 | 0.56 | 1.39 | 0.60 | 0.08 | 0.09 | NB* |

* no binding

Figure 4

| Antibody | Isotype | Linear | E2-CD81 | Genotypes | | | | | | |
|---|---|---|---|---|---|---|---|---|---|---|
| | | | | 1a* | 1b | 2a | 2b | 3A | 4 | 5 | 6 |
| CBH-4B | IgG1 κ | + | - | + | + | + | + | + | + | + | + |
| CBH-4D | IgG1 λ | + | - | + | + | + | + | + | - | + | + |
| CBH-4G | IgG1 κ | + | - | + | + | + | + | + | - | + | + |

*Binding by indirect immunofluorescent assay against HCV E1E2 transfected cells

Figure 5

| | Domain A | | | | | | | Domain B | | Domain C | | Domain D | | |
| --- | --- | --- | --- | --- | --- | --- | --- | --- | --- | --- | --- | --- | --- | --- |
| | CBH-4D | CBH-4G | CBH-4B | CBH-20 | CBH-21 | CBH-22 | | HC-1 | HC-11 | CBH-7 | CBH-23 | HC84.20 | HC84.24 | HC84.26 |
| I622A | 122 | 137 | 125 | 126 | 126 | 122 | | 111 | 130 | 120 | 95 | 130 | 135 | 109 |
| N623A | 15 | | 21 | 18 | 16 | 36 | | 42 | 21 | 47 | 55 | 26 | 38 | 55 |
| Y624A | 8 | | 18 | 19 | 15 | 16 | | 34 | 20 | 32 | 47 | 23 | 28 | 25 |
| T625A | 36 | 35 | 40 | 41 | 39 | 41 | | 64 | 38 | 93 | 89 | 44 | 48 | 83 |
| I626A | | 27 | 37 | 22 | 21 | 41 | | 69 | 28 | 39 | 78 | 58 | 55 | 67 |
| F627A | 8 | | 1 | 1 | 2 | 8 | | 225 | 147 | 746 | 597 | | | 82 |
| K628A | 30 | 54 | 49 | 50 | 46 | 46 | | 82 | 68 | 68 | 75 | 76 | 64 | 66 |
| V629A | 10 | 9 | 30 | 39 | 35 | 35 | | 103 | 96 | 186 | 134 | 69 | 65 | 67 |
| R630A | 8 | 58 | 22 | 67 | 65 | 64 | | 89 | 77 | 84 | 84 | 72 | 70 | 67 |
| M631A | 4 | 1 | 6 | 3 | 3 | 3 | | 76 | 49 | 76 | 70 | 77 | 73 | 77 |
| Y632A | 4 | 3 | 7 | 8 | 6 | 6 | | 92 | 67 | 281 | 212 | 91 | 93 | 86 |
| V633A | 10 | 10 | 11 | 22 | 16 | 8 | | 86 | 60 | 97 | 94 | 76 | 77 | 78 |
| G634A | 40 | 62 | 78 | 69 | 65 | 64 | | 93 | 77 | 90 | 106 | 83 | 77 | 79 |
| G635A | 56 | 43 | 50 | 65 | 60 | 60 | | 88 | 66 | 109 | 90 | 73 | 68 | 64 |

Legend: 21-40% | 41-60% | 61-100% | >100%

RATIONAL VACCINE DESIGN FOR HEPATITIS C VIRUS

CROSS REFERENCE

This application claims benefit of U.S. Provisional Patent Application No. 61/882,508, filed Sep. 25, 2013, which applications are incorporated herein by reference in their entirety.

GOVERNMENT RIGHTS

This invention was made with Government support under contract AI081903 awarded by the National Institutes of Health. The Government has certain rights in the invention.

BACKGROUND

Up to 170 million people worldwide are chronically infected with HCV, with many at significant risk for cirrhosis, liver failure and hepatocellular carcinoma. The World Health Organization estimates an annual increase in the global burden by 2 million new infections (Shepard et al. (2005) Lancet Infect Dis 5:558-567). Efforts at vaccine development have yet to succeed despite two decades of work. A key step towards reaching this goal is to identify and exploit relevant mechanisms of immune protection. Although there are no clearly established in vitro correlates of protective immunity, multiple lines of evidence suggest that CD4+ and CD8+ T cell responses, while critical for controlling acute HCV infection, are inadequate for prevention of long-term persistence in most infected individuals (Bowen et al. (2005) Nature 436:946-952). Emerging evidence supports the importance of virus-neutralizing (Vn) antibodies, and the ability of B cell responses to modify the course of infection.

The development of in vitro cell culture models, based on HCV retroviral pseudotype particles expressing E1E2 (HCVpp) and infectious cell culture-derived HCV virions (HCVcc), has facilitated the measurement of antibody-mediated virus neutralization, and thus to evaluate the impact of antibody in the control of infection (Bartosch et al. (2003) J Exp Med 197:633-642, Cai et al. (2005) J Virol 79:13963-13973, Hsu et al. (2003) Proc Natl Acad Sci USA 100:7271-7276, Lindenbach et al. (2005) Science 309:623-626, Wakita et al. (2005) Nat Med 11:791-796, Zhong et al. (2005) Proc Natl Acad Sci USA 102:9294-9299). Chimpanzee studies have shown that protection from an infectious HCV inoculum with HCV-specific IgG is correlated with antibody titers blocking infection of target cells with HCVpp (Bartosch et al. (2003) Proc Natl Acad Sci USA 100:14199-14204). Control of virus infection and the Vn antibody response measured via HCVpp have been associated in single source outbreaks of acute HCV infection (Lavillette et al. (2005) J Virol 79:6023-6034, Pestka et al. (2007) C. Proc Natl Acad Sci USA 104:6025-6030), and confirmed in a study of active injection drug users (Osburn et al. (2010) Gastroenterology 138:315-324). While only 25% of subjects in this study cleared primary HCV infection, 83% cleared re-infection, and clearance in some subjects was associated with cross-reactive Vn antibodies.

In addition, antibodies to HCV E2 prevent infection in a human liver-mouse chimeric model (Law et al. (2008) Nature Medicine 14:25-27, Meuleman et al. (2008) Hepatology 48:1761-1768). Finally, an immunocompetent humanized mouse model for HCV exhibited a robust antibody response to a recombinant vaccinia virus expressing HCV proteins that protected against a heterologous infectious HCV challenge in some of the animals, which was correlated with the serum level of antibodies to E2 (Dorner et al. (2011) Nature 474:208-211).

A significant challenge for vaccine development is defining conserved epitopes that i) are capable of eliciting protective antibodies in this highly diverse virus, and ii) are resistant to development of escape mutants. Treatment of HCV and the development of vaccines that broadly protect against highly diverse HCV genotypes and subtypes are of interest in the field. The present invention addresses this issue.

SUMMARY OF THE INVENTION

Compositions and methods are provided relating to human anti-HCV vaccines for prophylaxis against infection with different genotypes and subtypes of HCV. HCV E2 glycoprotein, which is the major target of neutralizing antibody response to virus, is modified to enhance the protective immune response. Such modified polypeptides are typically at least about 50 amino acids of contiguous E2 sequence, at least about 100 amino acids, at least about 200 amino acids, up to substantially all of the E2 protein. These polypeptides find use in screening assays, generation of monoclonal antibodies, and in vaccines. For the purposes of discussion, reference is made to the sequence of HCV set forth in SEQ ID NO:1, which provides an exemplary polyprotein from HCV, also shown in FIG. 1, where the E2 protein extends from amino acids 394-746. The modifications to the E2 polypeptide described herein can be utilized in various formats and within the context of different HCV E2 genotypes.

In some embodiments of the invention, a modified HCV E2 polypeptide is provided. In other embodiments, a polynucleotide encoding such a modified HCV E2 polypeptide is provided. The polypeptide and/or the nucleic acid can be used in the formulation of a vaccine, e.g. a virus-like particle, a recombinant protein vaccine which can be formulated with an adjuvant, a vector vaccine, and the like. In some embodiments, a vaccine formulation comprising a polypeptide or a polynucleotide of the invention is provided.

HCV E2 polypeptides of the invention comprise one or more of the following modifications: a) insertion of N-glycans to mask less desirable epitopes; b) complete or partial deletion of HVR1; c) elimination of specific N-glycans to up-regulate B cell response to epitopes not associated with viral escape; and d) specific amino acid substitution at contact residues within epitopes that are associated with viral escape. In some embodiments, all of the modifications (a) to (d) are introduced in the HCV E2 polypeptide. In other embodiments, one or more modifications from each group are introduced. In other embodiments, one or more modifications from a single group, from two groups, or from 3 groups are introduced. Such modifications, alone or in combination, may be combined with substitution of residue Y632 with alanine, serine, etc., to further silent epitopes associated with non-neutralizing antibodies.

Specifically, (a) highly immunodominant epitopes that are associated with viral escape or non-neutralizing antibodies can be masked so as to focus an immune response (i.e., to enhance the immunoprominence of an epitope) to epitopes that are less immunodominant, but which are essential for virus entry and therefore are less likely to be altered in virus escape mutation and selection. In this modification, an N-glycan is inserted at 437 and one or more in the segment encompassing 622 to 634, and preferentially at 627 and 631

(relative to SEQ ID NO:1, shown in FIG. 1). Amino acid modifications to effect this change are substitution of the amino acid present at one more or residues 437, 627 and 631 with asparagine, e.g. W437N, F627N and M631N substitutions; and introduction of a serine or threonine at one or more of residues 439, 629 and 633, e.g. A439T, A439S; V629T, V629S; and/or V633T, V633S to generate a motif for N-glycosylation. In certain embodiments, the combined amino acid changes are introduction of 437N and 439$^T/_S$; 627N and 629$^T/_S$; and/or 631N and 633$^T/_S$. Polypeptides incorporating these changes are expressed in a cell that provides for correct N-glycosylation, including without limitation mammalian cells.

Modification (b) provides for a partial or complete deletion of the HVR1 region. Where the deletion is complete, amino acids 384-409 (relative to SEQ ID NO:1, shown in FIG. 1) are deleted from the polypeptide. When the deletion is partial, amino acids 384-404 (relative to SEQ ID NO:1, shown in FIG. 1) are deleted from the polypeptide. The partial deletion allows maintenance of HVR1 reactivity to SR-B1, which segment may be involved in eliciting antibodies that are able to block cell-to-cell transmission of HCV.

Modification (c) provides for elimination of one or more N-glycans, generally by substitution of an asparagine residue with a glutamine residue, although less conservative substitutions or deletions can also be made, e.g. deletion of the asparagine residue, substitution of asparagine with other amino acids, e.g. alanine, glycine, serine, etc. Asparagine residues of interest for substitution are N417, N423, N448, and N532. In certain embodiments, the amino acid substitutions are one or more of N417Q, N423Q, N448Q and N532Q. The elimination of these glycans allows increased antibody elicitation to the regions of Q412-N423; N434-K446; and D520-N540, respectively.

Modification (d) masks the immunogenic residue E431 by substituting the native amino acid with alanine, serine, etc. to silence a specific epitope associated with viral escape. In specific embodiments, the amino acid substitution is selected from E431A, E431S and E431G.

Other aspects and features will be readily apparent to the ordinarily skilled artisan upon reading the present disclosure.

BRIEF DESCRIPTION OF THE DRAWINGS

The invention is best understood from the following detailed description of exemplary embodiments when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not necessarily to-scale. On the contrary, the dimensions of the various features are arbitrarily expanded or reduced for clarity. Included in the drawings are the following figures:

FIG. 3. Binding affinity (kD nM) to HCV E1E2 with or without HVR1.

FIG. 4. Binding by non-neutralizing antigenic domain A antibodies to different HCV genotypes.

FIG. 5. Antigenic Domain A epitope mapping in an E2 segment unique to domain A. Summary of epitope location for antigenic domain A. E2 mutant proteins were expressed in 293T cells and cell lysates were analyzed by ELISA. Each test HMAb was tested at 2 µg/ml. Individual protein expression was normalized by binding of CBH-17, an HCV E2 HMAb to a linear epitope. Representative domain B, C and D are as indicated. Red indicates 0-20%, orange 21-40%, brown 41-60%.

DETAILED DESCRIPTION OF THE EMBODIMENTS

Figure 1:
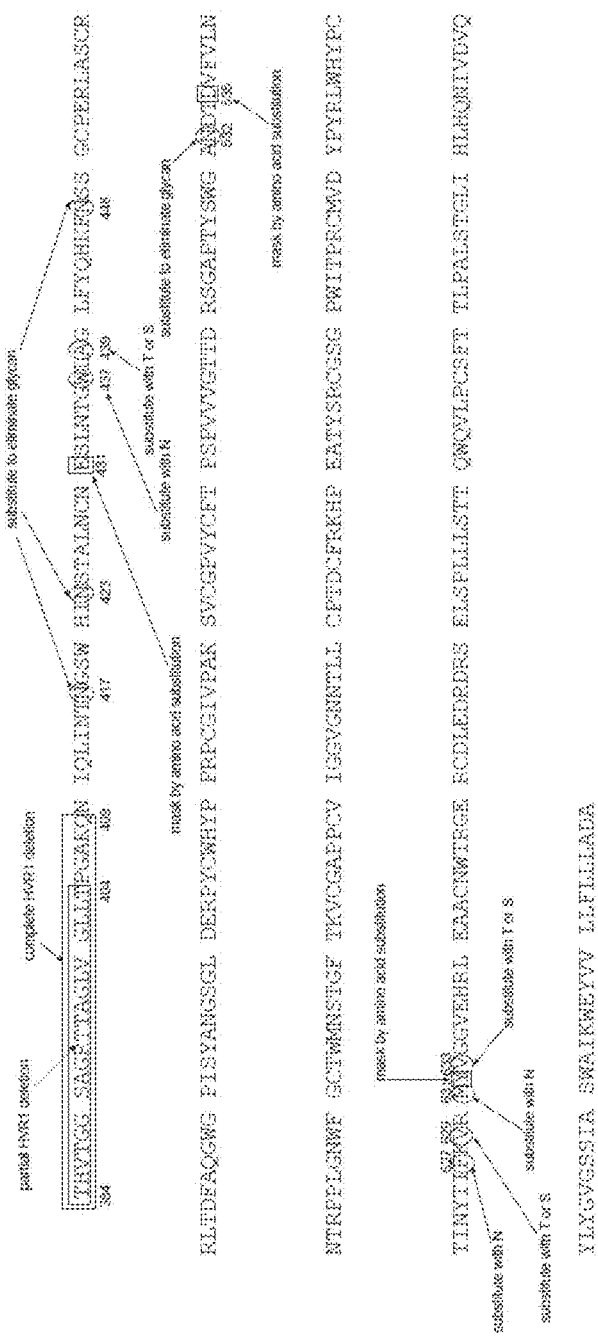
FIG. 1. Sites of amino acid modifications (SEQ ID NO:1).

It is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "Flaviviridae virus" or "flavivirus" is meant any virus from the Flaviviridae family, including those viruses that infect humans and non-human animals. The polynucleotide and polypeptides sequences encoding these viruses are well known in the art, and may be found at NCBI's GenBank database, e.g., as Genbank Accession nos. NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety. In general the term "flavivirus" includes any member of the family Flaviviridae, including, but not limited to, Dengue virus, including Dengue virus 1, Dengue virus 2, Dengue virus 3, Dengue virus 4 (see, e.g., GenBank Accession Nos. M23027, M19197, A34774, and M14931); Yellow Fever Virus; West Nile Virus; Japanese Encephalitis Virus; St. Louis Encephalitis Virus; Bovine Viral Diarrhea Virus (BVDV); and Hepatitis C Virus (HCV); and any serotype, strain, genotype, subtype, quasispecies, or isolate of any of the foregoing. Where the flavivirus is HCV, the HCV is any of a number of genotypes, subtypes, or quasispecies, including, e.g., genotype 1, including 1a and 1b, 2, 3, 4, 6, etc. and subtypes (e.g., 2a, 2b, 3a, 4a, 4c, etc.), and quasispecies.

The terms "hepatitis C virus," "HCV," "non-A non-B hepatitis," or "NANBH" are used interchangeably herein, and include any "genotype" or "subgenotype" (also termed "subtype") of the virion, or portion thereof (e.g., a portion of the E2 protein of genotype 1a of HCV), that is encoded by the RNA of hepatitis C virus or that occurs by natural allelic variation. The HCV genome comprises a 5'-untranslated region that is followed by an open reading frame (ORF) that codes for about 3,010 amino acids. The ORF runs from nucleotide base pair 342 to 8,955 followed by another untranslated region at the 3' end. The amino acids are subdivided into ten proteins in the order from 5' to 3' as follows: C; E1; E2; NS1; NS2; NS3; NS4 (a and b); and NS5 (a and b). These proteins are formed from the cleavage of the larger polyprotein by both host and viral proteases. The C, E1, and E2 proteins are structural and the NS1-NS5 proteins are nonstructural proteins. The C region codes for the core nucleocapsid protein. E1 and E2 are glycosylated envelope proteins that coat the virus. NS2 may be a zinc metalloproteinase. NS3 is a helicase. NS4a functions as a serine protease cofactor involved in cleavage between NS4b and NS5a. NS5a is a serine phosphoprotein whose function is unknown. The NS5b region has both RNA-dependent RNA polymerase and terminal transferase activity.

There are about six distinct HCV genotypes (e.g., genotypes 1, 2, 3, 4, 5, and 6) that are categorized by variations in the core protein and over 80 subgenotypes which exhibit further variation within each genotype, some of which include: 1a; 1b; 1c; 2a; 2b; 2c; 3a; 3b; 4a; 4b; 4c; 4d; 4e; 5a; and 6a. As a reference, the amino acid sequence of genotype 1, isolate 1a H77C (Genbank AF009606) is provided as SEQ ID NO:1, and modifications to the sequence are made with reference to SEQ ID NO:1. It will be understood by one of skill in the art that corresponding modifications are readily made in other HCV genotypes, by modifying the residue that corresponds to the named position in SEQ ID NO:1. Generally, the mature E2 protein corresponds to amino acid residues 384-746 of SEQ ID NO:1.

As used herein, the terms "neutralizes HCV," "inhibits HCV," and "blocks HCV" are used interchangeably to refer to the ability of an antibody of the invention to prevent HCV from infecting a given cell.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

"Polypeptide" and "protein" as used interchangeably herein, can encompass peptides and oligopeptides. Where "polypeptide" is recited herein to refer to an amino acid sequence of a naturally-occurring protein molecule, "polypeptide" and like terms are not necessarily limited to the amino acid sequence to the complete, native amino acid sequence associated with the recited protein molecule, but instead can encompass biologically active variants or fragments, including polypeptides having substantial sequence similarity or sequence identify relative to the amino acid sequences provided herein. In general, fragments or variants retain a biological activity of the parent polypeptide from which their sequence is derived.

As used herein, "polypeptide" refers to an amino acid sequence of a recombinant or non-recombinant polypeptide having an amino acid sequence of i) a native polypeptide, ii) a biologically active fragment of an polypeptide, or iii) a biologically active variant of an polypeptide. Polypeptides suitable for use can be obtained from any species, e.g., mammalian or non-mammalian (e.g., reptiles, amphibians, avian (e.g., chicken)), particularly mammalian, including human, rodent (e.g., murine or rat), bovine, ovine, porcine, murine, or equine, particularly rat or human, from any source whether natural, synthetic, semi-synthetic or recombinant. In general, polypeptides comprising a sequence of a human polypeptide are of particular interest.

The term "derived from" indicates molecule that is obtained directly from the indicated source (e.g., when a protein directly purified from a cell, the protein is "derived from" the cell) or information is obtained from the source, e.g. nucleotide or amino acid sequence, from which the molecule can be synthesized from materials other than the source of information.

The term "isolated" indicates that the recited material (e.g., polypeptide, nucleic acid, etc.) is substantially separated from, or enriched relative to, other materials with which it occurs in nature (e.g., in a cell). A material (e.g., polypeptide, nucleic acid, etc.) that is isolated constitutes at least about 0.1%, at least about 0.5%, at least about 1% or at least about 5% by weight of the total material of the same type (e.g., total protein, total nucleic acid) in a given sample.

The terms "subject" and "patient" are used interchangeably herein to mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest. As will be evidence from the context in which the term is used, subject and patient refer to a subject or patient susceptible to infection by a Flaviviridae virus, particularly HCV.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds calculated in an amount sufficient to produce the desired effect in association with a pharmaceutically acceptable diluent, carrier or vehicle. The specifications for the novel unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is usually free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Unless specifically indicated to the contrary, the term "conjugate" as described and claimed herein is defined as a heterogeneous molecule formed by the covalent attachment of one or more polypeptide fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by cell culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, may be made by recombinant DNA methods, including without limitation yeast display.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

By the term "vaccine" as used herein, is meant a composition; a formulation comprising a modified polypeptide of the invention; a virus or virus-like particle comprising a modified polypeptide of the invention complex; or a DNA encoding a modified polypeptide of the invention complex, which, when administered to a subject, induces cellular or humoral immune responses as described herein.

Some embodiments of the invention provide a method of stimulating an immune response in a mammal, which can be a human or a preclinical model for human disease, e.g. mouse, ape, monkey etc. "Stimulating an immune response" includes, but is not limited to, inducing a therapeutic or prophylactic effect that is mediated by the immune system of the mammal. More specifically, stimulating an immune response in the context of the invention refers to eliciting cellular or humoral immune responses, thereby inducing downstream effects such as production of antibodies, antibody heavy chain class switching, maturation of APCs, and stimulation of cytolytic T cells, T helper cells and both T and B memory cells.

As appreciated by skilled artisans, vaccine compositions are suitably formulated to be compatible with the intended route of administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH of the composition can be adjusted with acids or bases, such as hydrochloric acid or sodium hydroxide. Systemic administration of the composition is also suitably accomplished by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

Vaccine compositions may include an aqueous medium, pharmaceutically acceptable inert excipient such as lactose, starch, calcium carbonate, and sodium citrate. Vaccine compositions may also include an adjuvant, for example Freud's adjuvant. Vaccines may be administered alone or in combination with a physiologically acceptable vehicle that is suitable for administration to humans. Vaccines may be delivered orally, parenterally, intramuscularly, intranasally or intravenously. Oral delivery may encompass, for example, adding the compositions to the feed or drink of the mammals. Factors bearing on the vaccine dosage include, for example, the weight and age of the mammal. Compositions for parenteral or intravenous delivery may also include emulsifying or suspending agents or diluents to control the delivery and dose amount of the vaccine.

The modified polypeptides of the invention and polynucleotides that encode such modified polypeptides can be used in various HCV vaccine formulations known in the art, as a substitution for the wild-type HCV E2 sequence.

HCV vaccines include, without limitation, formulation of isolate polypeptides, e.g. E2 alone or in combination with E1 as separate molecules or as heterodimeric E1E2, and an adjuvant. A protein complex of HCV proteins, including E2 of the present invention, can be formulated with T-cell adjuvant immunostimulating complex matrix (IMX). The polypeptides of the invention can be fragmented to generate a peptide vaccine, e.g. administered with poly-L-arginine, can be formulated as a vaccine. Polynucleotides encoding the modified polypeptides of the invention can be administered in plasmid form, in a virus genome, including adenovirus, alphaviruses, canary pox, ovine atadenovirus and semliki-like viral particles. Advances in molecular virology have enabled the manipulation of viruses for delivery of foreign genetic material to mammalian cells. Their highly evolved mechanisms for cell entry and gene expression within the host cell remain intact and viral vectors can be rendered non-pathogenic and non-replicative by deletions at specific locus.

In some embodiments, the polypeptides of the invention are formulated for vaccine delivery as virus-like particles (VLPs).

Adenoviral (Ad) vectors are the best characterised viral vectors and have emerged as the most potent at T-cell priming in non-human primates (NHPs) and humans. Ad-based vaccines are particularly attractive gene vehicles as they can stably express large foreign inserts (~10 kbp), they remain epichromosomal and can be easily rendered replication defective by deletion of the E1 locus.

Other definitions of terms appear throughout the specification.

Polypeptide and Polynucleotide Compositions

The application discloses herein a modified HCV E2 polypeptide, which is altered from the wild-type in various ways to increase desired immune responses, which generate neutralizing antibodies across multiple HCV genotypes; and the reduce undesirable immune responses that are readily avoided by escape mechanisms. These modified polypeptides find use in screening assays, generation of monoclonal antibodies, and in vaccines.

All or a portion of the HCV E2 protein is provided, e.g. as the full-length E2 protein, or a modified peptide derived therefrom, including peptides comprising residues 420, 428, 429, 437, 441, 442, 443, 446, 613 and 616 of HCV E2 protein, where the epitope is of sufficient length to provide for binding specificity substantially similar to the specificity of binding to the native protein, e.g. a peptide of at least 20 amino acids, at least 30 amino acids, at least 40 amino acids, at least 50 amino acids, at least 100 amino acids, at least 150 amino acids, at least 200 amino acids up to the full length of the E2 protein, where the peptide may be a contiguous or non-contiguous sequence of an HCV E2 protein.

Peptides can be produced using techniques well known in the art. Such techniques include chemical and biochemical synthesis. Examples of techniques for chemical synthesis of peptides are provided in Vincent, in Peptide and Protein Drug Delivery, New York, N.Y., Dekker, 1990. Examples of techniques for biochemical synthesis involving the introduction of a nucleic acid into a cell and expression of nucleic acids are provided in Ausubel, Current Protocols in Molecular Biology, John Wiley, and Sambrook, et al in Molecular Cloning, A Laboratory Manual, Cold Spring Harbor Laboratory Press, 1989.

HCV E2 polypeptides of the invention comprise one or more of the following modifications: a) insertion of N-glycans to mask less desirable epitopes; b) complete or partial deletion of HVR1; c) elimination of specific N-glycans to up-regulate B cell response to epitopes not associated with viral escape; and d) specific amino acid substitution at contact residues associated with viral escape. In some embodiments, all of the modifications (a) to (d) are introduced in the HCV E2 polypeptide. In other embodiments, one or more modifications from each group are introduced. In other embodiments, one or more modifications from a single group, from two groups, or from 3 groups are introduced. Such modifications, alone or in combination, may be combined with substitution of residue at Y632 with alanine, serine, etc.

In certain embodiments a complete or partial deletion of HVR1 is combined with one or more glycan modifications as set forth in (a) and (c), and may be further combined with substitution of E431, as set forth in modification (d).

In modification (a), highly immunodominant residues are masked so as to generate an immune response to residues that are less immunodominant, but which are essential for virus function and therefore are less likely to be altered in virus escape mutation and selection. In this modification, an N-glycan is inserted at 437 and one or more in the segment encompassing 622 to 634, and preferentially at 627 and 631 (relative to SEQ ID NO:1, shown in FIG. 1). Amino acid modifications to effect this change are substitution of the amino acid present at one more or residues 437, 627 and 631 with asparagine, e.g. W437N, F627N and M631N substitutions; and introduction of a serine or threonine at one or more of residues 439, 629 and 633, e.g. A439T, A439S; V629T, V629S; and/or V633T, V633S to generate a motif for N-glycosylation. In certain embodiments, the combined amino acid changes are introduction of 437N and $439^{T/S}$; 627N and $629^{T/S}$; and/or 631N and $633^{T/S}$. Polypeptides incorporating these changes are expressed in a cell that provides for correct N-glycosylation, including without limitation mammalian cells.

Modification (b) provides for a partial or complete deletion of the HVR1 region. Where the deletion is complete, amino acids 384-409 (relative to SEQ ID NO:1, shown in FIG. 1) are deleted from the polypeptide. When the deletion is partial, amino acids 384-404 (relative to SEQ ID NO:1, shown in FIG. 1) are deleted from the polypeptide. The partial deletion allows maintenance of HVR1 reactivity to SR-B1, which segment may be involved in eliciting antibodies that are able to block cell-to-cell transmission of HCV.

Modification (c) provides for elimination of one or more N-glycans, generally by substitution of an asparagine residue with a glutamine residue, although less conservative substitutions or deletions can also be made, e.g. deletion of the asparagine residue, substitution of asparagine with other amino acids, e.g. alanine, glycine, serine, etc. Asparagine residues of interest for substitution are N417, N423, N448, and N532. In certain embodiments, the amino acid substitutions are one or more of N417Q, N423Q, N448Q and N532Q. The elimination of these glycans allows increased antibody elicitation to the regions of Q412-N423; N434-K446; and D520-N540, respectively.

Modification (d) masks the immunogenic residue E431 by substituting the native amino acid with alanine, serine, etc. In specific embodiments, the amino acid substitution is selected from E431A, E431S, E431G.

The invention also provides isolated nucleic acids encoding the modified HCV E2 polypeptide, vectors and host cells comprising the nucleic acid, and recombinant techniques for the production of the modified polypeptide. As is known in the art, various polynucleotides can be devised with respect to codon usage to produce a desired polypeptide, and one of skill in the art can readily generate a polynucleotide sequence that encodes a modified E2 protein. As an optional starting point, the sequence of isolates, 1a H77C (Genbank AF009606) and 1bSF (Genbank JN118490) can be used, without limitation. In some embodiments a contiguous nucleotide sequence is at least about 20 nt., at least about 25 nt, at least about 50 nt., at least about 75 nt, at least about 100 nt, and up to the complete coding sequence may be used.

For recombinant production of the modified polypeptide, the nucleic acid encoding it is inserted into a replicable vector for further cloning (amplification of the DNA) or for expression. DNA encoding the modified polypeptide is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The modified polypeptides of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2).

Host cells are transformed with the above-described expression or cloning vectors for modified polypeptide production and cultured in conventional nutrient media modified as appropriate for inducing promoters, selecting transformants, or amplifying the genes encoding the desired sequences.

The modified polypeptide composition prepared from the cells can be purified using, for example, hydroxylapatite chromatography, gel electrophoresis, dialysis, and affinity chromatography, and the like as known in the art. For example, antibodies against E2 protein can be used as affinity reagents for purification. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In some embodiments of the invention, the modified polypeptide(s) are used in a screening method to select for antibodies optimized for affinity, specificity, and the like. In such screening methods, random or directed mutagenesis is utilized to generate changes in the amino acid structure of the variable region or regions, where such variable regions will initially comprise one or more of the provided CDR sequences, e.g. a framework variable region comprising CDR1, CDR2, CDR3 from the heavy and light chain sequences. Methods for selection of antibodies with optimized specificity, affinity, etc., are known and practiced in the art, e.g. including methods described by Presta (2006) Adv Drug Deliv Rev. 58(5-6):640-56; Levin and Weiss (2006) Mol Biosyst. 2(1):49-57; Rothe et al. (2006) Expert Opin Biol Ther. 6(2):177-87; Ladner et al. (2001) Curr Opin Biotechnol. 12(4):406-10; Amstutz et al. (2001) Curr Opin Biotechnol. 12(4):400-5; Nakamura and Takeo (1998) J Chromatogr B Biomed Sci Appl. 715(1):125-36 each herein specifically incorporated by reference for teaching methods of mutagenesis selection. Such methods are exemplified by Wu et al. (2005) J. Mol. Biol. (2005) 350, 126-144.

In other embodiments, the modified polypeptide of the invention is used as an immunogen, including without limitation vaccine preparation.

Methods of Use

In the methods disclosed herein, an immunologically effective amount of one or more modified polypeptides of the invention, which may be conjugated to a suitable carrier molecule, polynucleotides encoding such modified polypeptides, including viral vectors, are administered to a patient by administrations of a vaccine, in a manner effective to result in an improvement in the patient's condition. successive, spaced In an exemplary embodiment, of carrier proteins represented by virus capsid proteins that have the capability to self-assemble into virus-like particles (VLPs) are utilized in combination with the modified polypeptide of the invention. Examples of VLPs used as peptide carriers are hepatitis B virus surface antigen and core antigen, hepatitis E virus particles, polyoma virus, bovine papilloma virus, and the like.

In another embodiment, modified polypeptides of the invention are coupled to one of a number of carrier molecules, known to those of skill in the art. A carrier protein must be of sufficient size for the immune system of the subject to which it is administered to recognize its foreign nature and develop antibodies to it.

In some cases the carrier molecule is directly coupled to the immunogenic peptide. In other cases, there is a linker molecule inserted between the carrier molecule and the immunogenic peptide. For example, the coupling reaction may require a free sulfhydryl group on the peptide. In such cases, an N-terminal cysteine residue is added to the peptide when the peptide is synthesized. In an exemplary embodiment, traditional succinimide chemistry is used to link the peptide to a carrier protein. Methods for preparing such peptide:carrier protein conjugates are generally known to those of skill in the art and reagents for such methods are commercially available (e.g., from Sigma Chemical Co.). Generally about 5-30 peptide molecules are conjugated per molecule of carrier protein.

Exemplary carrier molecules include proteins such as keyhole limpet hemocyanin (KLH), bovine serum albumin (BSA), flagellin, influenza subunit proteins, tetanus toxoid (TT), diphtheria toxoid (DT), cholera toxoid (CT), a variety of bacterial heat shock proteins, glutathione reductase (GST), or natural proteins such as thyroglobulin, and the like. One of skill in the art can readily select an appropriate carrier molecule. In some cases, the carrier molecule is a non-protein, such as Ficoll 70 or Ficoll 400 (a synthetic copolymer of sucrose and epichlorohydrin), a polyglucose such as Dextran T 70.

A peptide vaccine composition may comprise single or multiple copies of the same or different modified polypeptide of the invention. In one aspect of this embodiment, the peptide vaccine composition may contain different immunogenic peptides with or without flanking sequences, combined sequentially into a polypeptide and coupled to the same carrier. Alternatively, immunogenic peptides, may be coupled individually as peptides to the same or a different carrier, and the resulting immunogenic peptide-carrier conjugates blended together to form a single composition, or administered individually at the same or different times.

In general, peptide vaccine compositions are administered with a vehicle. The purpose of the vehicle is to emulsify the vaccine preparation. Numerous vehicles are known to those of skill in the art, and any vehicle which functions as an effective emulsifying agent finds utility in the present invention. To further increase the magnitude of the immune response resulting from administration of the vaccine, an immunological adjuvant may be included in the vaccine formulation. Exemplary adjuvants known to those of skill in the art include water/oil emulsions, non-ionic copolymer adjuvants, e.g., CRL 1005 (Optivax; Vaxcel Inc., Norcross, Ga.), aluminum phosphate, aluminum hydroxide, aqueous suspensions of aluminum and magnesium hydroxides, bacterial endotoxins, polynucleotides, polyelectrolytes, lipophilic adjuvants and synthetic muramyl dipeptide (norMDP) analogs.

Suitable pharmaceutically acceptable carriers for use in an immunogenic proteinaceous composition of the invention are well known to those of skill in the art. Such carriers include, for example, phosphate buffered saline, or any physiologically compatible medium, suitable for introducing the vaccine into a subject.

Numerous drug delivery mechanisms known to those of skill in the art may be employed to administer the immunogenic peptides of the invention. Controlled release preparations may be achieved by the use of polymers to complex or absorb the peptides or antibodies. Controlled delivery may accomplished using macromolecules such as, polyesters, polyamino acids, polyvinyl pyrrolidone, ethylenevinylacetate, methylcellulose, carboxymethylcellulose, or protamine sulfate, the concentration of which can alter the rate of release of the peptide vaccine.

In some cases, the peptides may be incorporated into polymeric particles composed of e.g., polyesters, polyamino acids, hydrogels, polylactic acid, or ethylene vinylacetate copolymers. Alternatively, the peptide vaccine is entrapped in microcapsules, liposomes, albumin microspheres, microemulsions, nanoparticles, nanocapsules, or macroemulsions, using methods generally known to those of skill in the art.

In some embodiments, the vaccine is a vector. As used herein, a "vector" is a tool that allows or facilitates the transfer of an entity from one environment to another. In one example, the techniques and products described in U.S. Pat. No. 5,990,091, International Publication Nos. WO 99/60164 and WO98/00166, van Ginkel et al., "Adenoviral gene delivery elicits distinct pulmonary-associated T helper cell responses to the vector and to its transgene," *J Immunol* 159(2):685-93, 1997; and Osterhaus et al, "Vaccination against acute respiratory virus infections and measles in man," *Immunobiology* 184(2-3):180-92, 1992, which contain information concerning expressed gene products, antibodies and uses thereof, vectors for in vivo and in vitro expression of exogenous nucleic acid molecules, promoters for driving expression or for operatively linking to nucleic acid molecules to be expressed, method and documents for producing such vectors, compositions comprising such vectors or nucleic acid molecules or antibodies, dosages, and modes and/or routes of administration (including compositions for nasal administration), inter alia, can be employed in the practice of this invention and are incorporated by herein reference in their entireties.

The vector can be a viral vector, a bacterial vector, a protozoan vector, a retrotransposon, a transposon, a virus shell, or a DNA vector. In another aspect, the viral vector, the bacterial vector, the protozoan vector and the DNA vector can be recombinant vectors. The vector can be an adenovirus. In one example, the adenovirus recombinant can include E1-defective, E3-defective, and/or E4-defective adenovirus vectors, or the "gutless" adenovirus vector, where all viral genes are deleted. Specific sequence motifs such as the RGD motif can be inserted into the H-I loop of an adenovirus vector to enhance its infectivity. An adenovirus recombinant is constructed by cloning specific transgenes or fragments of transgenes into any of the adenovirus vectors such as those described above. In one example, the adenovirus recombinant can be used to transduce epidermal or mucosal cells of a subject in a noninvasive mode for use as an immunizing agent. In one example, the adenovirus vector can be defective in its E1 region. In another example, the adenovirus vector can be defective in its E3 region. In a further example, the adenovirus vector can be defective in its E1 and E3 regions. In another example, the DNA is in plasmid form.

A vaccine of the present invention can be administered to patient by different routes such as intravenous, intraperitoneal, subcutaneous, intramuscular, or orally. A preferred route is intramuscular or oral. Suitable dosing regimens are preferably determined taking into account factors well known in the art including age, weight, sex and medical condition of the subject; the route of administration; the desired effect; and the particular conjugate employed (e.g., the peptide, the peptide loading on the carrier, etc.). The vaccine can be used in multi-dose vaccination formats.

The timing of doses depend upon factors well known in the art. After the initial administration one or more booster doses may subsequently be administered to maintain antibody titers. An example of a dosing regime would be a dose on day 1, a second dose at or 2 months, a third dose at either 4, 6 or 12 months, and additional booster doses at distant times as needed.

In one aspect, the invention provides a means for classifying the immune response to peptide vaccine, e.g., 9 to 15 weeks after administration of the vaccine; by measuring the level of antibodies against the immunogenic peptide of the vaccine.

Formulations

The vaccine formulations of the present invention may be used in immunization for the various HCV associated diseases. In some embodiments, the recipient is at a high risk of infection.

The vaccine formulation is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the vaccine formulation is suitably administered by pulse infusion, particularly with declining doses of the vaccine.

For the prevention or treatment of disease, the appropriate dosage of vaccine will depend on the type of disease to be treated, the severity and course of the disease, whether the vaccine is administered for preventive purposes, previous therapy, the patient's clinical history and response to the vaccine, and the discretion of the attending physician. The vaccine is suitably administered to the patient at one time or over a series of treatments.

In another embodiment of the invention, an article of manufacture containing materials useful for the vaccination described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is one or more antibodies in a formulation of the invention as described above. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Therapeutic formulations are prepared for storage by mixing the vaccine having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The vaccine composition will be formulated, dosed, and administered in a fashion consistent with good medical practice. The "therapeutically effective amount" of the vaccine to be administered will be governed by clinical considerations, and is the minimum amount necessary to reduce virus titer in an infected individual.

One may adjust dosage based on the amount of peptide delivered. An immunologically effective dose is one that stimulates the immune system of the patient to establish a level immunological memory sufficient to provide long term protection against disease caused by infection with HCV. More precise dosages should be determined by assessing the immunogenicity of the vaccine produced so that an immunologically effective dose is delivered.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of vaccine fragments, or in the use of vaccine conjugates. The dosage may also be varied for localized administration, or for systemic administration, e.g. i.m., i.p., i.v., and the like.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

Where the formulation is an aqueous suspension, such can contain the active agent in a mixture with a suitable excipient(s). Such excipients can be, as appropriate, suspending agents (e.g., sodium carboxymethylcellulose, methylcellulose, hydropropyl-methylcellulose, sodium alginate, polyvinylpyrrolidone, gum tragacanth and gum acacia); dispersing or wetting agents; preservatives; coloring agents; and/or flavoring agents.

Suppositories, e.g., for rectal administration of agents, can be prepared by mixing the agent with a suitable non-irritating excipient that is solid at ordinary temperatures but liquid at the rectal temperature and will therefore melt in the rectum to release the drug. Such materials include cocoa butter and polyethylene glycols.

The invention now being fully described, it will be apparent to one of ordinary skill in the art that various changes and modifications can be made without departing from the spirit or scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Protective B and T cell responses are implicated in immunity against hepatitis C virus (HCV). Virus-neutralizing (Vn) antibodies have been shown to play a key role in protection from HCV in humans. However, HCV has devised a variety of strategies to evade this protective B cell response that involve masking of broadly Vn epitopes, sets of immunodominant Vn epitopes associated with rapid escape mutations, and a set of immunodominant non-neutralizing epitopes. Based on a body of evidence in the literature and our own studies with panels of human Vn antibodies, including identified epitopes that are resistant to virus escape, a rationally designed vaccine, based on the expression of broadly conserved epitopes mediating virus neutralization and minimal expression of epitopes associated with virus escape mutations or non-Vn antibodies, will provide protection against a broad range of HCV genotypes and subtypes.

Characterization of multiple panels of human monoclonal antibodies (HMAbs) to HCV has revealed the existence of multiple immunogenic domains or clusters of overlapping epitopes, at least four of which mediate broad Vn by blocking E2 binding to CD81, an essential co-receptor for HCV entry (Keck et al. (2008) J Virol 82:6061-6066, Keck et al. (2007) J Virol 81:1043-1047).

Hypervariable region 1. The envelope glycoproteins of HCV display some of the highest levels of genetic diversity found in HCV, with E2 more variable than E1. A major determinant of Vn is HVR1, consisting of the first 26 amino acids (aa 384-409) located at the N-terminus of E2, which is highly immunogenic. Antibodies against HVR1 can be detected in the majority of HCV infected individuals (Ray et al. (2010 J Infect Dis 202:862-866, Zibert et al. (1997) Arch Virol 142:523-534, Zibert et al. (1995) Virology 208:653-661). Animals immunized with synthetic HVR1 peptide elicit high titer serum antibodies to HVR1 (Shimizu et al. (1996) Virology 223:409-412, Zucchelli et al. (2001) Hepatology 33:692-703). However, antibodies to HVR1 over time drive replication of resistant viral variants (Farci et al. (1994) Proc Natl Acad Sci USA 91:7792-7796, Kato et al. (1993) J Virol 67:3923-3930, Weiner et al. (1992) Proc Natl Acad Sci USA 89:3468-3472). Studies of individuals progressing from the acute phase of infection to chronicity confirmed both the relationship between Vn antibodies and virus clearance, and escape from Vn secondary to HVR1 variants (Dowd et al. (2009) Gastroenterology 136:2377-2386, von Hahn et al. (2007) Gastroenterology 132:667-678). High-titer serum Vn antibodies were detected in individuals with spontaneous resolution of infection, peaking at the time of viral clearance, while most individuals progressing to chronic infection demonstrated low-titer or absent Vn antibodies throughout early acute infection. When patient-specific HCVpp expressing sequential envelope variants were used to assess Vn by autologous sera, Vn of earlier sequence variants was detected prior to later variants, indicating clearance and evolution of quasispecies variants in response to pressure from Vn antibodies.

Site directed mutagenesis of the pseudotyped envelope sequence revealed amino acid substitutions within HVR1 that were responsible for the loss of Vn sensitivity over time. One interpretation of these findings is that Vn antibodies directed at more conserved epitopes outside of HVR1 occur later in the course of infection. Interestingly, viral particles without HVR1, delta (Δ) HVR1, are more sensitive to antibody-mediated Vn, which indicates that HVR1 partly shields more conserved epitopes mediating Vn (Bankwitz et al. (2010) J Virol 84:5751-5763, Prentoe et al. (2011) 85:2224-2234). Finally, in an E1E2 glycoprotein vaccine human study whereby an antibody response to HVR1 was a dominant component (21/41 of vaccinated volunteers), only 11/21 of HVR1-reactive sera contained a measurable Vn activity (Ray et al. (2010) J Infect Dis 202:862-866, Zibert et al. (1997) Arch Virol 142:523-534; Zibert et al. (1995) Virology 208:653-661).

Taken together, these data indicate that the HVR1 region encoding immunodominant epitopes serves as a decoy, diverting away and shielding the immune response from more conserved Vn epitopes. For these reasons, a vaccine candidate will be a ΔHVR1 HCV VLP. However, a concern is that the elimination of HVR1 will affect the native structure of the HCV E1E2 heterodimer or viral particles. Although the deletion of HVR1 led to a virus that remained infectious, the infectivity of ΔHVR1 HCVcc was reduced (Bankwitz et al. (2010) J. Virol., 84: 5751-5763). This finding raises the possibility of an adverse impact on the native structure of HCV. FIG. 3 shows binding affinities of a panel of antibodies to conformational epitopes on E2 to a HCVpp construct without HVR1 and with HVR1. Binding by these antibodies are improved indicating that deletion of HVR1 will not adversely impact the native structure of the virus.

Broadly neutralizing, conformation-dependent epitopes. The majority of antibodies with broad Vn activity recognize conformational epitopes involving conserved residues on E2 (Allander et al. (2000) J Gen Virol 81:2451-2459, Bugli et al. (2001) J Virol 75:9986-9990, Habersetzer et al. (1998) Virology 249:32-41, Hadlock et al. (2000) J Virol 74:10407-10416, Keck et al. (2008) J Virol 82:6061-6066, Law et al. (2008) Nature Medicine 14:25-27). We have described panels of Vn and non-Vn HMAbs to conformational epitopes on HCV E2. Competition analyses delineated at least five immunogenic clusters of overlapping epitopes with distinct functions and properties (Keck et al. (2005) J Virol 79:13199-13208, Keck et al. (2004) J Virol 78:9224-9232). Vn HMAbs segregated into four clusters, designated as antigenic domains B, C, D and HC33 that inhibited E2 binding to the HCV co-receptor, CD81 (Keck et al. (2008) J Virol 82:6061-6066, Keck et al. (2007) J Virol 81:1043-1047). Non-Vn HMAbs fell into one cluster designated as antigenic domain A (Keck et al. (2005) J Virol 79:13199-13208, Keck et al. (2004) J Virol 78:9224-9232).

Antibody response to the epitopes within antigenic domain A and others that are also non-neutralizing is likely to be a significant part of the response to HCV infection (Burioni et al. (2004) Virology 327:242-8). Antigenic domain A antibodies are broadly reactive to different HCV genotypes and subtypes, as shown by indirect immunofluorescent assay (FIG. 4).

Epitope mapping by alanine scanning identified a segment on E2 encompassing 622-633 that is unique to domain A epitopes and not shared with antigenic domains B, C and D (FIG. 5). Consequently, the insertion of multiple N-glycans in this region, and more specifically at 627 and 631, could mask the antigenic domain A epitopes from the antibody response.

Antigenic domain B HMAbs displayed varying degrees of Vn activity in assays with HCVpp containing E1E2 of HCV genotypes 1 to 6. Alanine scanning revealed that two conserved E2 residues at G530 and D535 are required for binding by all domain B HMAbs and some at 529 (Keck et al. (2008) J Virol 82:6061-6066, Owsianka et al. (2008) J. Gen Virol 89:653-659). Importantly, G530 and D535 have been also shown to participate in E2 binding to CD81 (Owsianka et al. (2006) J Virol 80:8695-8704).

The data thus demonstrate that antigenic domain B HMAbs exert broad Vn effects on HCV by competing with CD81 for binding to conserved residues on E2 that are important for viral entry. Consistent with this, broadly Vn HMAbs derived from combinatorial libraries isolated from individuals with chronic HCV also recognize epitopes containing W529, G530 and D535. The conserved nature of this cluster of overlapping epitopes makes them of interest for vaccine development. Of concern, however, single amino acid substitutions can lead to virus escape from some domain B-reactive antibodies, recapitulating the escape observed with antibodies directed against the HVR1 domain (Keck et al. (2008) J Virol 82:6067-6072, von Hahn et al. (2007) Gastroenterology 132:667-678). CBH-2 is a HMAb recognizing a broadly conserved epitope in domain B that contains residues G530 and D535. However, a single amino acid substitution at residue 431 results in complete escape from CBH-2. In addition, we reported on three patterns of virus response to immune pressure by propagating an infectious cell culture virus (HCVcc) in the presence of a Vn domain B antibody (Keck et al. (2011) J Virol 85:10451-10463). Of the three tested antigenic domain B antibodies, one antibody led to escape mutant viruses without affecting viral fitness. A second led to escape but with compromised viral fitness, and a third led to complete virus elimination without escape mutants. These findings collectively highlight the rarity of antigenic domain B viral epitopes that are both conserved and not associated with virus escape. Epitope mapping and virus co-culture studies of multiple domain B HMAbs revealed two regions spanning 425-443 and 529-535 that are involved in their respective epitopes (Keck et al. (2011) J Virol 85:10451-10463). Domain B antibodies associated with viral escape will tend to have contact residues within 425-443 as well as to 529-535. The rare antigenic domain B antibodies not associated with viral escape will have contact residues more restricted to the 529-535 region (Keck et al. (2011) J Virol 85:10451-10463). An insertion of an N-glycan at 437 partly masks the elicitation of antigenic domain B antibodies associated with viral escape.

Figure 6:
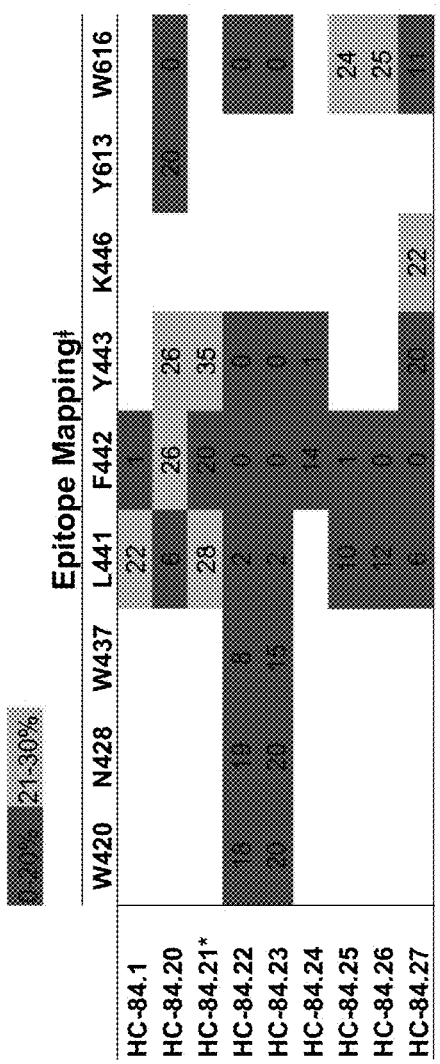
FIG. 6. Summary of epitope location for each HC-84 antibody. E2 mutant proteins were expressed in 293T cells and cell lysates were analyzed by ELISA. Each HC-84 HMAb was tested at 2 µg/ml. Individual protein expression was normalized by binding of CBH-17, and HCV E2 HMAb to a linear epitope. Contact residues for HC-84.21 are based on antibody binding at 0.1 µg/ml. Red indicates 0-20%, orange 21-40%, brown 41-60%.

We isolated two additional panels of broadly neutralizing antibodies that are relevant for vaccine design (Keck et al. (2012) J Virol, doi:10.1128/JVI.01941-12, Keck et al. (2012) PLoS Pathog 8:e 1002653). The first panel, designated as HC84-related or antigenic domain D antibodies, neutralized HCVcc with genotypes 1-6 envelope proteins with varying profiles (Keck et al. (2012) J Virol, 1941-12, Keck et al. (2012) PLoS Pathog 8:e 1002653), and each inhibited E2 binding to the viral receptor CD81. Interestingly, when a 2a HCVcc isolate was passaged in the presence of each of these antigenic domain D antibodies, viral escape was not observed. Consequently, an effective HCV vaccine should direct the antibody response to antigenic domain D epitopes. Epitope mapping of domain D HMAbs revealed a cluster of contact residues in an E2 segment encompassing 441-443 (FIG. 6). Since an N-glycan is located near this region at N448, the elimination of this glycan will up-regulate the antibody response to antigenic domain D epitopes.

Figure 7:
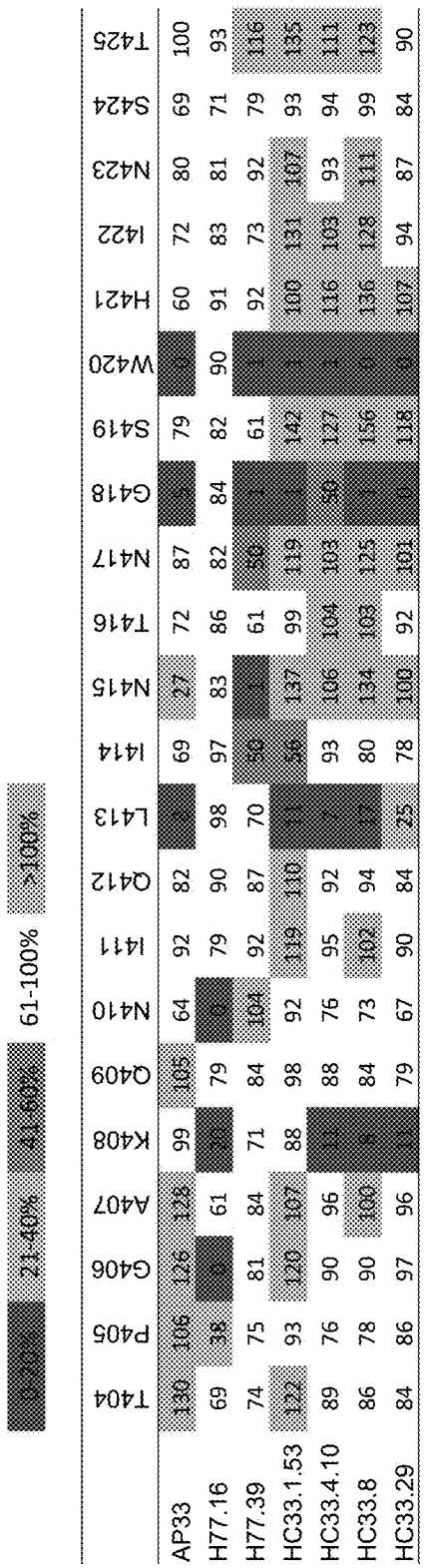
FIG. 7. Epitope mapping of rodent and human monoclonal antibodies to a conserved region on E2 located at amino acid 410-425. Summary of epitope location for antibodies to HVR1 and a conserved region, aa410-425. E2 mutant proteins were expressed in 293T cells and cell lysates were analyzed by ELISA. Each test Mab was tested at 2 µg/ml. Individual protein expression was normalized by binding of CBH-17, and HCV E2 HMAb to a linear epitope. Red indicates 0-20%, orange 21-40%, brown 41-60% AP33, H77.16 and H77.39 are mouse Mabs. All three antibodies inhibit virus binding to CD81. H77.16 and H77.39 also inhibit virus binding to SR-B1. The HC33-related antibodies are human Mabs and they all inhibit virus binding to CD81. HC33.4 blocks H77.16 binding to E2 by 70% and HC33.1.53 blocks H77.16 by 40%.

The second panel, designated as HC33-related HMAbs, is directed at a region known to encode conserved epitopes located at an E2 sequence encompassing aa 412-423 (Owsianka et al. (2005) J Virol 79:11095-11104, Tarr et al. (2006) Hepatology 43:592-601). We isolated multiple HMAbs that neutralized HCVcc of different genotypes and subtypes with different profiles and potency, and inhibited E2 binding to CD81 (Keck et al. (2013) J. Virol 87(1):37). Interestingly, some of the HC33-related HMAbs mapping revealed a contact residue within HVR1 at 408 (FIG. 7). A mouse neutralizing antibody, designated as H77.16 is known to contain a contact residue at 408 that mediates neutralization by inhibiting E2 binding to CD81 and SR-B1 (Sabo et al. (2011) J. Virol. 85:7005-7019). Consequently, the inclusion of aa 405-409 will induce HC33-like antibodies that have a contact residue at 408. Moreover, these antibodies are likely to mediate neutralization by inhibiting E2 binding to both CD81 and SR-B1.

In summary, large panels of broadly Vn antibodies to distinct regions on the E2 glycoproteins have been produced that guide the rational design on prototype HCV VLP-based vaccines. Epitopes (e.g., CBH-2) that are associated with escape by site-directed mutagenesis will be silenced.

Negative Modulators of Vn Activity.

Glycosylation of the virus envelope, non-Vn antibodies or virion-associated lipoproteins may interfere with antibody-mediated Vn by masking Vn epitopes or otherwise limiting access of Vn antibodies to their cognate epitopes (Falkowska et al. (2007) J Virol 81:8072-8079, Helle et al. (2007) J Virol 81:8101-8111, Thomssen et al. (1992) Med Microbiol Immunol (Berl) 181:293-300, Zhang et al. (2007) Proc Natl Acad Sci U SA 104:8449-8454, Zhang et al. (2009) Proc Natl Acad Sci USA 106:7537-7541). Studies with HCVpp indicated that N-linked glycans at conserved Asn residues of the E2 protein hindered Vn activities of HCV-specific polyclonal sera, as well as Vn HMAbs (Falkowska et al. (2007) J Virol 81:8072-8079, Helle et al. (2007) J Virol 81:8101-8111). HC33-related antibodies have contact residues at 413, 418 and 420; antigenic domain D HMAbs have contact residues at 441, 442 and 443; and B HMAbs have contact residues at 529, 530 and 535. Four conserved N-glycans are located near these regions, N417, N423, N448 and N532. The elimination of these N-glycans by substitutions at 417, 423, 448 and 532, will lead to an improved HCV immunogen to elicit HC33-like, antigenic domain D-like and those antigenic domain B-like antibodies that are not associated with viral escape, as shown for a specific N-glycan on HIV gp120 (Li et al. (2008) J Virol 82:638-651).

Clusters of Broadly Virus Neutralizing Antibodies:

The rational design of an HCV vaccine requires information on epitopes that mediate broad Vn against different HCV genotypes and subtypes. B-cell conformational epitopes on HCV E2 are organized in discrete immunogenic clusters or domains. Non-Vn epitopes are in one cluster, designated as antigenic domain A. Vn epitopes are in multiple clusters, with one highly immunogenic cluster, designated as antigenic domain B. Epitope mapping revealed that all antigenic domain A HMAbs shared a contact residue at Y632 and all antigenic domain B HMAbs shared a contact residue at D535. A screening algorithm was developed for new HMAbs to E2 that minimized the selection of non-Vn domain A antibodies and Vn antibodies to domain B by employing E2 mutants shown not to bind to domain A or domain B HMAbs. We also implemented a new approach to isolate HMAbs by yeast surface display library of single chain variable fragments (scFvs). Nine scFvs were selected based on broad binding to genotype 1-6 E2 proteins and converted to $IgG_1$.

Selection, Production, and Characterization of Rationally Designed HCV VLP.

The most common HCV genotype associated with chronic hepatitis in the US is genotype 1. The 1a H77C (Genbank AF009606) is considered as the model vaccine. Binding kinetics of selected antigenic domain B (CBH-5, HC-1 and HC-11), domain C (CBH-7, CBH-23, (41), domain D (HC84.1, HC84.20, HC84.23, HC84.24, HC84.26), and HC33-related (HC33.1.53, HC33.4.10) are measured against 1a H77C HCVpp. The selected HMAbs are the ones with the broadest and most potent Vn activities, and many of them are not associated with viral escape when co-cultured with a 2a HCVcc isolate. Moreover, their epitopes collectively span the entire E2 glycoprotein and outside of HVR1.

Model HCV VLP Vaccine Employing a Retroviral HCVpp Backbone.

HVR1 serves as a decoy that diverts and shields the Vn response from more conserved epitopes. Deletion of HVR1 in a 2a HCVcc isolate led to enhanced neutralization activities by our domain B and C HMAbs. This is supported by increased binding by domains A, B, C HMAbs to a ΔHVR1 1a H77C E2 construct compared to wt E2. ΔHVR1 1a and 1b HCVpp are constructed and compared with wt HCVpp $K_D$ values by the panel of selected domains B, C, D and HC33-related HMAbs. $K_D$ measurements on partially purified sucrose cushioned HCVpp are determined by ELISA and surface plasmon resonance in a BIAcore 3000. An immunogenicity study is performed in mice with the two HCVpp constructs to ensure that the immunogen with the ability to induce the best neutralizing response is selected. The ΔHVR1 HCVpp isolate having the broadest and highest $K_D$ values and strongest immunogenicity will serve as the prototype immunogen for further modifications.

A series of N-glycan substitution mutants are constructed on the selected ΔHVR1 HCVpp to assess their ability to further enhance the exposure of conserved Vn epitopes on E2. Our entire panel of Vn HMAbs mediates Vn by blocking E2 binding to CD81. The location of their collective E2 contact residues are in proximity to four N-glycans at E2N1 (N417), E2N2 (N423), E2N4 (N448) and E2N6 (N532). These N-glycans have been shown to negatively modulate Vn activities of domains B and C HMAbs and E2 binding to CD81. Glutamine substitution at each of these sites led to HCVpp and HCVcc mutants with enhanced binding to CD81 and higher susceptibility to Vn antibodies. N-glycan (glutamine) substitution mutants will be constructed singly and in combination to assess $K_D$ and Vn by the panel of Vn HMAbs. The combination having the most improvements in $K_D$ values and Vn potencies, as determined by $IC_{50}$, will be the prototype HCVpp to model baculovirus expressed VLP.

Construction of HCV VLP Vaccine Candidates.

The wild type and ΔHVR1 VLPs is generated using HCV core as supporting matrix. The particles are evaluated for yield based on total E1/E2 content, homogeneity by electron microscopy (EM), and for binding to the panel of HMAbs and CD81 using ELISA. Consequently, 2-3 E2 variants are inserted into the VLP construct and VLPs for each mutant are generated. The immunogen candidates are thoroughly characterized in vitro. A Bac-To-Bac Baculovirus Expression System (Invitrogen) can be used generate the VLPs. pFastBac bacmids are generated expressing E1, E2, and HCV core. The bacmid is transfected into Sf9 insect cells to produce recombinant baculoviruses (rBV). rBVs are then used to infect Sf9 cells, which will then produce the VLPs. VLPs are purified using sucrose gradient centrifugation from cells lysed in a mild detergent. Chromatography methods based on anion exchange can be used to further reduce the rBV contamination. This chromatography step will be applied if more than 10% rBV is observed. For generation of the mutants the basic E1/E2/Core-pFastBac plasmid cassette is mutated by replacement of gene segments or PCR-assisted point mutations as needed and respective rBV and VLPs are produced.

In Vitro Characterization of HCV Vaccine Candidates.

Baculovirus expressed VLP candidates are evaluated in vitro. In addition to measuring $K_D$ with the panel of Vn HMAbs, efficiency of binding to CD81 is determined by ELISA. This will provide an additional level of support of structural integrity of the VLP vaccine candidates. Heterodimer formation is determined using non-reducing SDS-PAGE with and without boiling of samples. The homogeneity of the VLP is determined using electron microscopy. Furthermore, limited biophysical characterization is performed. Thermal stability of the VLPs is assessed by Thermofluor (also called as Differential Scanning Fluorimetry or DSF) experiments using Sypro Orange as the external fluorescent probe which binds to hydrophobic residues detecting exposure of hydrophobic residues during protein unfolding reflected in increased fluorescence. Thermal denaturation pattern of the mutant VLPs is compared with that of wt to ensure that mutation did not compromise the structural integrity of the proteins.

Immunogenicity and Efficacy of HCV Vaccine Candidates in Mice.

BALB/c mice are vaccinated with varied doses of designed VLP vaccine in adjuvant or the wild-type (wt) VLP vaccine as control. Induction of antibodies to broadly conserved epitopes mediating Vn, HVR1, and epitopes mediating non-Vn antibodies are compared between wt and designed vaccine candidates. Vn titers against cell culture infectious HCV (HCVcc) with genotypes 1-6 envelope proteins are evaluated as proof of concept study.

Mouse Immunogenicity Study:

Groups of 10 BALB/c mice (6-8 weeks old) are vaccinated three times at 2 week intervals with wt or each of up to three HCV-VLP candidates at two doses of 20 and 100 μg or 20 μg of Ebola virus VLPs (eVLPs) as control along with adjuvant. Mice are bled on days 0, 14, 28 and 42 (terminal bleed) to test the kinetics and quality of the antibody response. As adjuvant, the clinical stage adjuvant IDC-1001 (Immune Design Corp.) is used, a glucopyranosyl lipid A based toll-like receptor-4 agonist. This glucopyranosyl lipid-based adjuvant is known to induce a Th2 biased immune response.

Characterization of the Immune Response:

The key response is virus neutralization. $IC_{50}$ values of sera from vaccinated mice is determined against 1a H77C and 2a HCVcc, and the breadth of neutralizing activity is determined against a panel of HCVcc expressing genotypes 1-6 E1E2. In addition, the total antibody response to E1 and E2 is determined by ELISA. A competition study against directly labeled CBH-2 and domain A HMAbs provides information on the extent that these antibodies will or will not be induced. Avoidance of HVR1 antibodies is determined by binding studies against HVR1 peptides. Finally, the ability of the mouse sera to inhibit binding of wt HCVpp to CD81 is tested by ELISA. A final candidate is selected for advanced preclinical development including efficacy studies in nonhuman primates to assess the breadth and depth of the vaccine-induced antibody response, in vivo protection studies in a human-mouse chimeric liver model for HCV, and process development for production of clinical material for safety and immunogenicity testing, generation of VLP and cell banks, as well as development of supportive identity, purity, and potency assays.

Example 2

Effects of Anti-HVR1 Modulating the Protective B Cell Response

In addition to the genetic mutation escape strategy from Vn antibodies, HCV has other evasion mechanisms to negatively modulate the Vn antibody response. Glycosylation of the virus envelope, serum high density lipoprotein (HDL) or virion-associated lipoproteins may interfere with antibody-mediated Vn by masking Vn epitopes or otherwise limiting access of Vn antibodies to their cognate epitopes (Falkowska et al. 2007. J Virol 81:8072-8079; Goffard et al. 2005 J. Virol. 79:8400-8409; Helle et al. 2007 J Virol 81:8101-8111; Helle et al. 2010 J Virol 84:11905-11915).

In addition, it has been proposed that epitopes located in a segment of E2 encompassing aa434-446, named epitope-II, elicit non-Vn antibodies and that these antibodies interfere with the Vn activities of antibodies directed at an adjacent E2 segment encompassing aa412-426, named epitope-I (Duan et al. 2012 J Virol 86:12686-12694; Zhang et al. 2007 Proc Natl Acad Sci USA 104:8449-8454; Zhang et al. 2009 Proc Natl Acad Sci USA 106:7537-7541).

However, other studies employing similar approaches of isolating polyclonal antibodies to synthetic peptides encompassing aa412-426 and aa434-446 showed no interference in Vn (Tarr et al. 2012 J Virol 86:2739-2749). Because of the importance of conserved epitopes within aa412-423 in vaccine development, we isolated and characterized a panel of HMAbs to this region, designated as HC33-related antibodies (antigenic domain E) (Keck et al. 2013 J Virol 87:37-51). Since antigenic domain D has contact residues within aa434-446, we assessed whether domain D and E Vn HMAbs were antagonistic, synergistic or additive by the median-effect analysis method, as described by Chou and Talalay (1984 Adv Enzyme Regul 22:27-55) using the CompuSyn software (ComboSyn Inc, Paramus, N.J.).

The approach takes into account the potency, the shape and the slope of the dose-dependent Vn curve of each antibody alone and in combination, at a constant ratio, to calculate a combination index (CI). A CI value of 1 indicates additive effect, <1 indicates synergism and >1 indicates antagonism. For each antibody, dose-dependent Vn is measured initially to determine the concentration that results in 50% reduction in FFU ($IC_{50}$ value). The constant ratio of the combined antibodies is set by the $IC_{50}$ values of the two antibodies. Vn of a serial two-fold dilution of each antibody and in combination is then measured in a range of concentrations above and below the $IC_{50}$ values. The measured neutralization values are entered in the program as fractional effect (FA) in the range 0.01<FA<0.99 for each of the two antibodies and in combination. The software determines the linear correlation coefficient, r, of each curve to indicate the fit or conformity of the data with respect to the median-effect method and calculates the CI values in relation to FA values.

The overall effect was additive Vn, which indicated that antibodies to aa412-423 and aa434-446 do not hinder their respective Vn activities. In our studies, non-Vn HC33 antibodies were identified. However, they were of lower affinities and when the affinity of a non-Vn HC33 HMAb was increased by affinity maturation, Vn activity was restored. This is an explanation for a non-Vn murine MAb to epitope-II that has been reported, since this antibody is of a lower affinity.

Figure 2:
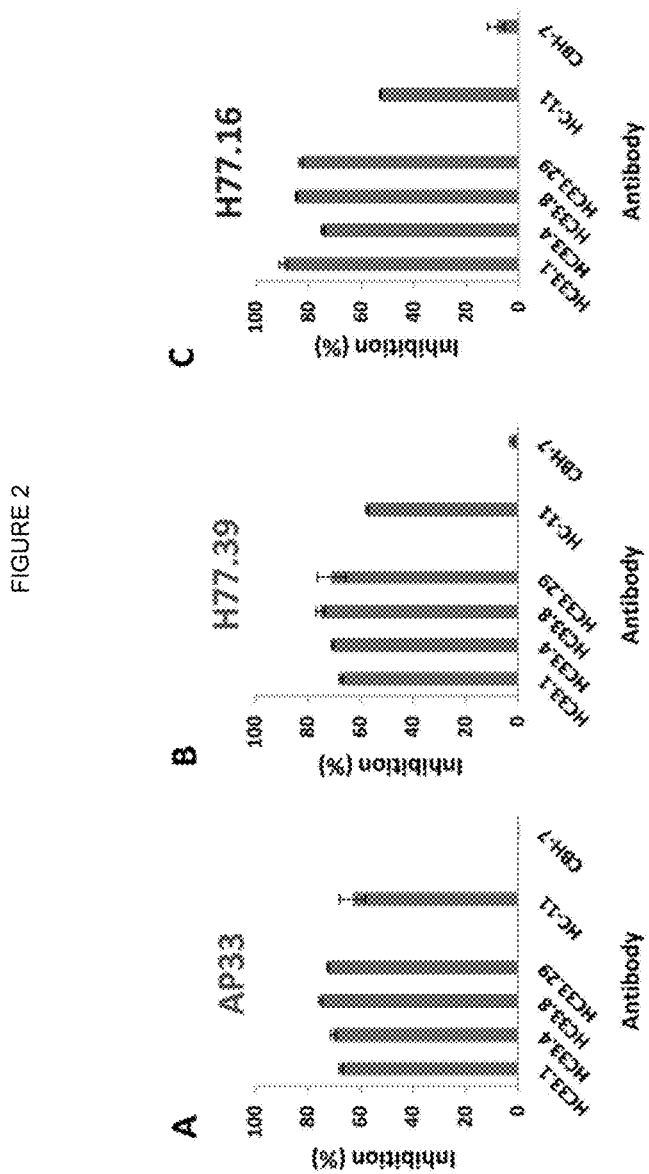
FIG. 2. Competitive binding by murine MAbs to aa412-423 and to HVR1. Each murine antibody at 20 µg/ml was incubated for 30 min. with GNA captured H77C E2 prior to adding each tested HMAb at 1 µg/ml. Binding by HMAbs was analyzed by ELISA. Data are shown as mean values of two experiments performed in triplicates.

Epitope mapping of antigenic domain E (HC33 HMAbs) revealed two subgroups. One subgroup, e.g., HC33.1, has contact residues similar to murine MAbs to this region, AP33 and H77.39 (103, 114) that are restricted to aa412-423 (domain E). The other subgroup, e.g., HC33.4, included a contact residue within HVR1 located at 408. This raised the possibility of anti-HVR1 antibodies interfering with the functions of antibodies to aa412-423. As expected, AP33 and H77.39 inhibited the binding of both subgroups of HC33 HMAbs (FIGS. 2A and B).

Inhibition was also observed against a Vn domain B HMAb, HC-11, but not a Vn domain C HMAb, CBH-7. Surprisingly, H77.16, a murine MAb to 1a H77C HVR1 also inhibited all HC33 HMAbs and HC-11, but not CBH-7 (FIG. 7C). By the median-effect analysis method, Vn was tested for each HC33.1, HC33.4, HC-11 or CBH-7 by itself and in combination with H77.16, as described above and employing H77 HCVcc (Ma et al. 2008 J Virol 82:7624-7639; Yi et al. 2007 J Virol. 81:629-638). The calculated combination index values at different fractional effect values were indicative of antagonism. Tabulated in Table 6, moderate antagonism (defined as 1.2-1.45) was observed between H77.16 and HC33.1. Stronger antagonism with average CI value of 2.97 was observed between H77.16 and HC33.4. Additive cooperativity (defined as 0.9-1.1) was observed between H77.16 and CBH-7, which is consistent with the lack of competition between these two antibodies (FIG. 2C).

TABLE 6

Combination Index for virus neutralization

| Antibody Combination | CI Values | | | |
|---|---|---|---|---|
| | $ED_{50}$ | $ED_{75}$ | $ED_{90}$ | Average |
| HC33.1 + H77.16 | 1.56 | 1.34 | 1.24 | 1.38 |
| HC33.4 + H77.16 | 1.84 | 2.76 | 4.32 | 2.97 |
| HC-11 + H77.16 | 1.44 | 1.48 | 1.59 | 1.50 |
| CBH-7 + H77.16 | 1.01 | 1.01 | 1.01 | 1.01 |

Taken together, the relationship between HVR1 with domains B and E is a prime example of an immunogenic decoy. HVR1 diverts the immune response away from conserved domain B and E epitopes. While virtually all infected subjects continuously produce anti-HVR1, only 2-15% have antibodies to aa412-423 (Tarr et al. 2007 J Gen Virol 88:2991-3001; Tarr et al. 2012 J Virol 86:2739-2749). Moreover, HVR1 blunts the protective B cell response by a number of mechanisms. HVR1 conceals CD81 binding sites and blocks conserved Vn epitopes; elicits Vn antibodies associated with rapid escape throughout the course of infection; and finally the anti-HVR1 antibodies inhibit the binding by antibodies to domains B and E and interfere with their neutralizing activities. The last mechanism contributes to the progression of chronic infection with HCV since anti-HVR1 antibodies are continuously induced during the course of infection.

A similar mechanism may account for antigenic domain B antibodies that are associated with rapid escape, e.g., CBH-2 (Keck et al. 2008 J Virol 82:6067-6072), in their ability to interfere with other broadly Vn HMAbs within domains B (e.g., HC-1 and HC-11, and D. Interactions that are tested for this purpose include a) the interactions between Vn HMAbs within an antigenic domain; b) between Vn HMAbs from different domains; and c) between Vn and non-Vn HCV HMAbs. The non-Vn HMAbs at saturating antibody binding concentrations are tested to increase the $IC_{50}$ values of selected Vn HMAbs. Synergistic, additive or antagonistic cooperativity by two Vn antibodies will be evaluated by the median-effect analysis method that we have implemented (Keck et al. 2013 J Virol 87:37-51). The approach takes into account the potency, the shape and the slope of the dose-dependent neutralization curve of each antibody alone and in combination, at a constant ratio, to calculate a combination index (CI). A CI value of 1 indicates additive effect, <1 indicates synergism and >1 indicates antagonism. (d) The role of antibody affinity in determining Vn and non-Vn to the same site or region is explored by affinity maturation.

What is claimed is:

1. A modified Hepatitis C Virus (HCV) E2 polypeptide comprising an amino acid sequence aligning with SEQ ID NO:1, but numbered according to an E1-E2 polypeptide where residue 1 of SEQ ID NO:1 is numbered as residue 383; b) deletion of 384-409 or 384-404; and c) amino substitutions N417Q, N423Q, N448Q and N532Q.

2. The polypeptide of claim 1, further comprising substitution of the amino acid present at one more or residues 437, 627 and 631 with asparagine; and introduction of a serine or threonine at one or more of residues 439, 629 and 633.

3. The polypeptide of claim 1, further comprising an amino acid substitution selected from E431A, E431S, and E431G.

4. The polypeptide of claim 1, further comprising the amino acid modifications Y632A and D535A.

5. An immunogenic composition comprising:
   a modified HCV E2 polypeptide as set forth in claim 1; and
   a pharmaceutically acceptable excipient.

6. An immunogenic composition of claim 5, further comprising an adjuvant.

7. The immunogenic composition of claim 5, further comprising a virus-like particle.

* * * * *

SEQUENCE LISTING

```
<160> NUMBER OF SEQ ID NOS: 1

<210> SEQ ID NO 1
<211> LENGTH: 345
<212> TYPE: PRT
<213> ORGANISM: Hepatitis C virus

<400> SEQUENCE: 1

Thr His Val Thr Gly Gly Ser Ala Gly Arg Thr Thr Ala Gly Leu Val
1               5                   10                  15

Gly Leu Leu Thr Pro Gly Ala Lys Gln Asn Ile Gln Leu Ile Asn Thr
            20                  25                  30

Asn Gly Ser Trp His Ile Asn Ser Thr Ala Leu Asn Cys Asn Glu Ser
        35                  40                  45

Leu Asn Thr Gly Trp Leu Ala Gly Leu Phe Tyr Gln His Lys Phe Asn
    50                  55                  60

Ser Ser Gly Cys Pro Glu Arg Leu Ala Ser Cys Arg Arg Leu Thr Asp
65                  70                  75                  80

Phe Ala Gln Gly Trp Gly Pro Ile Ser Tyr Ala Asn Gly Ser Gly Leu
                85                  90                  95

Asp Glu Arg Pro Tyr Cys Trp His Tyr Pro Pro Arg Pro Cys Gly Ile
            100                 105                 110

Val Pro Ala Lys Ser Val Cys Gly Pro Val Tyr Cys Phe Thr Pro Ser
        115                 120                 125

Pro Val Val Val Gly Thr Thr Asp Arg Ser Gly Ala Pro Thr Tyr Ser
    130                 135                 140

Trp Gly Ala Asn Asp Thr Asp Val Phe Val Leu Asn Asn Thr Arg Pro
145                 150                 155                 160

Pro Leu Gly Asn Trp Phe Gly Cys Thr Trp Met Asn Ser Thr Gly Phe
                165                 170                 175

Thr Lys Val Cys Gly Ala Pro Pro Cys Val Ile Gly Gly Val Gly Asn
            180                 185                 190

Asn Thr Leu Leu Cys Pro Thr Asp Cys Phe Arg Lys His Pro Glu Ala
        195                 200                 205

Thr Tyr Ser Arg Cys Gly Ser Gly Pro Trp Ile Thr Pro Arg Cys Met
    210                 215                 220

Val Asp Tyr Pro Tyr Arg Leu Trp His Tyr Pro Cys Thr Ile Asn Tyr
225                 230                 235                 240

Thr Ile Phe Lys Val Arg Met Tyr Val Gly Gly Val Glu His Arg Leu
                245                 250                 255

Glu Ala Ala Cys Asn Trp Thr Arg Gly Glu Arg Cys Asp Leu Glu Asp
            260                 265                 270

Arg Asp Arg Ser Glu Leu Ser Pro Leu Leu Leu Ser Thr Thr Gln Trp
        275                 280                 285

Gln Val Leu Pro Cys Ser Phe Thr Thr Leu Pro Ala Leu Ser Thr Gly
    290                 295                 300

Leu Ile His Leu His Gln Asn Ile Val Asp Val Gln Tyr Leu Tyr Gly
305                 310                 315                 320
```

```
Val Gly Ser Ser Ile Ala Ser Trp Ala Ile Lys Trp Glu Tyr Val Val
            325                 330                 335

Leu Leu Phe Leu Leu Leu Ala Asp Ala
            340             345
```